United States Patent
Matsukura et al.

(10) Patent No.: US 9,279,795 B2
(45) Date of Patent: Mar. 8, 2016

(54) COMBUSTIBLE GAS DETECTING DEVICE

(71) Applicant: NGK SPARK PLUG CO., LTD., Nagoya-shi, Aichi-ken (JP)

(72) Inventors: Yusuke Matsukura, Nagoya (JP); Shoji Kitanoya, Kasugai (JP); Masaya Watanabe, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 344 days.

(21) Appl. No.: 13/942,147

(22) Filed: Jul. 15, 2013

(65) Prior Publication Data

US 2014/0020448 A1    Jan. 23, 2014

(30) Foreign Application Priority Data

Jul. 17, 2012    (JP) .................................. 2012-158277

(51) Int. Cl.
G01N 25/18 (2006.01)
G01N 33/00 (2006.01)
G01N 27/18 (2006.01)

(52) U.S. Cl.
CPC ............ *G01N 33/0036* (2013.01); *G01N 27/18* (2013.01)

(58) Field of Classification Search
CPC .................................................... G01N 25/18
USPC ................. 73/23.31, 25.01, 25.03, 25.05
See application file for complete search history.

(56) References Cited

U.S. PATENT DOCUMENTS

| | | | | |
|---|---|---|---|---|
| 2011/0199709 | A1* | 8/2011 | Ieda | ................................ 361/78 |
| 2011/0257897 | A1* | 10/2011 | Watanabe | ............ G01N 27/128 702/23 |
| 2012/0204623 | A1* | 8/2012 | Matsuno | ................ G01N 25/18 73/25.03 |
| 2012/0247184 | A1* | 10/2012 | Kitanoya | ............... G01N 27/18 73/25.05 |

FOREIGN PATENT DOCUMENTS

JP    4302611 B2 *    7/2009

* cited by examiner

*Primary Examiner* — Herzon E Williams
*Assistant Examiner* — Hoang Nguyen
(74) *Attorney, Agent, or Firm* — Sughrue Mion, PLLC

(57) ABSTRACT

A flammable gas concentration detection apparatus (1) including an energization control unit (50) that switches the energization state of heating resistor (34) at regular time periods TW, and a gas concentration computation unit (7). The heating resistor has first and second set temperatures CH and CL. The voltage detected across the heating resistor at the first and second set temperatures corresponds to a high and low temperature voltage, respectively. The gas concentration computation unit computes the concentration of a flammable gas based on a first information group including an average high temperature voltage averaging the values of two temporally successive high temperature voltages, the low temperature voltage in a period of time between two high temperature voltages, and an environment temperature in the period of time in which the low temperature voltage is detected.

2 Claims, 9 Drawing Sheets

COMBUSTIBLE GAS DETECTING DEVICE

TECHNICAL FIELD

The present invention relates to a flammable gas detection apparatus that detects the gas concentration of flammable gas that is present in an atmosphere for detection.

BACKGROUND ART

In recent years, due to societal demand for protection of environment and nature, research on fuel cells as a highly efficient and clean energy source is being actively conducted. Among others, expectations are growing for polymer electrolyte fuel cells (PEFC) and hydrogen internal combustion engines as an energy source for 0household and onboard purposes because of their advantages in low temperature operation and high output density.

In these systems, because hydrogen, which is a flammable gas, is used as fuel, for example, detection of gas leakage is cited as one of important issues.

In a known flammable gas detection apparatus for detecting the gas concentration of flammable gas of this type existing in an atmosphere for detection, a gas detection element is disposed in the atmosphere for detection, where the gas detection element is provided with a heating resistor whose resistance value is changed by its own temperature change (heat generation), and with a temperature-measuring resistor whose resistance value is changed by a change in environment temperature.

Specifically, in this flammable gas detection apparatus, the resistance value of the heating resistor of the gas detection element is controlled by a bridge circuit to have resistance values corresponding to two set temperatures (a first set temperature and a second set temperature), and the gas concentration is calculated by using a control voltage (voltage across the heating resistor) at the time and a voltage difference (temperature voltage) caused by a change in the resistance value of the temperature-measuring resistor.

Each of the set temperatures (the first set temperature and the second set temperature) is changed by selectively switching the conduction states of fixed resistors with different resistance values installed in the bridge circuit at regular periods of time, for example (see Patent Document 1, for example). Thus, the voltage across the heating resistor at the first set temperature and the second set temperature can be detected by using a single bridge circuit and heating resistor, whereby the size of the gas detection element can be decreased and power consumption can be suppressed.

Patent Document 1 describes that, in consideration of the variation of the concentration of the flammable gas in the atmosphere for detection depending on the humidity in the atmosphere for detection, in addition to the voltage difference, the ratio (voltage ratio) of the voltages across the heating resistor at the first set temperature and the second set temperature is computed, and the gas concentration is corrected by utilizing the fact that the ratio is substantially proportional to the humidity.

PRIOR ART DOCUMENT

Patent Document

[Patent Document 1] Japanese Patent No. 4302611

SUMMARY OF THE INVENTION

Problem to be Solved by the Invention

When, as described above, the single bridge circuit and heating resistor are used and the fixed resistors in the bridge circuit are switched at regular periods of time, the detection timing for the voltage across the heating resistor that is detected at the first set temperature on the high temperature side (hereinafter referred to as high temperature voltage "VH") and the detection timing for the voltage across the heating resistor that is detected at the second set temperature on the low temperature side (hereinafter referred to as low temperature voltage "VL") are displaced by the period of time. In this case, when the environment temperature is changed over time, the gas concentration detection accuracy is decreased by the displacement in detection timing between VH and VL.

Namely, as shown in FIG. 10, when the environment temperature is increased during detection, VH and VL are decreased over time (FIG. 10($a$), ($b$)). Thus, when VH1 is detected in the initial period of time TW1 (FIG. 10($c$)) and then VL1 is detected in the next period of time TW2, the value of the low temperature voltage becomes smaller compared with the case where the low temperature voltage (which is virtually denoted by "VL0'") is detected at the same detection timing (same period of time TW1) as for VH1. As a result, the voltage difference or the voltage ratio may have inaccurate values, resulting in a decrease in gas concentration detection accuracy.

Namely, an object of the present invention is to provide a flammable gas detection apparatus for suppressing the decrease in gas concentration detection accuracy accompanying the temporal change in environment temperature.

Means for Solving the Problems

In order to solve the above-described problem, a flammable gas detection apparatus according to the present invention includes a heating resistor disposed in an atmosphere for detection and whose resistance value is changed in response to a temperature change in the heating resistor; an energization control unit that performs control to switch an energization state of the heating resistor at regular periods of time so that the heating resistor has resistance values respectively corresponding to preset two set temperatures; a temperature-measuring resistor whose resistance value is changed by a change in an environment temperature which is the temperature in the atmosphere for detection; and a gas concentration computation unit that computes the concentration of a flammable gas in the atmosphere for detection by using a voltage across the heating resistor that is detected at the time of energization of the heating resistor by the control by the energization control unit, and the environment temperature based on a voltage change caused by a change in the resistance value of the temperature-measuring resistor. The two set temperatures include a first set temperature on a high temperature side and a second set temperature on a low temperature side. The voltage across the heating resistor that is detected at the first set temperature is a high temperature voltage, and the voltage across the heating resistor that is detected at the second set temperature is a low temperature voltage. The gas concentration computation unit computes the concentration of the flammable gas based on a first information group including an average high temperature voltage averaging the values of two temporally successive high temperature voltages; the low temperature voltage in a period of time between the two high temperature voltages; and the environment temperature in the period of time in which the low temperature voltage is detected, or a second information group including an average low temperature voltage averaging the values of two temporally successive low temperature voltages; the high temperature voltage in a period of time between the two low temperature voltages; and the environment temperature in the period of time in which the high temperature voltage is detected.

In the flammable gas detection apparatus in which the energization state of the heating resistor is switched so that resistance values respectively corresponding to two set temperatures at regular periods of time are obtained, the concentration of flammable gas is inevitably computed by detecting the high temperature voltage (or the low temperature voltage) in the initial period of time, and then detecting the low temperature voltage (or the high temperature voltage) in the next period of time. However, if the environment temperature is greatly changed over time, the gas concentration detection accuracy may be decreased by the displacement in detection timing between the high temperature voltage and the low temperature voltage.

Thus, in the flammable gas detection apparatus according to the present invention, an average high temperature voltage or an average low temperature voltage is used, so that the detection timing with the corresponding low temperature voltage or high temperature voltage can be virtually aligned, whereby the decrease in gas concentration detection accuracy accompanying a temporal change in environment temperature can be suppressed. It is necessary, in computation of the concentration of flammable gas, to also consider the environment temperature detected by the temperature-measuring resistor. However, by using the environment temperature in the period of time in which the low temperature voltage is detected for the first information group including the average high temperature voltage, while using the environment in the period of time in which the high temperature voltage is detected for the second information group including the average low temperature voltage, the decrease in gas concentration detection accuracy can be simply suppressed without the process of averaging the environment temperature, for example.

In the flammable gas detection apparatus, as the low temperature voltage in the first information group, the second one of the two temporally successive low temperature voltages in the second information group may be used, and, as the high temperature voltage in the second information group, the second one of the two temporally successive high temperature voltages in the first information group may be used.

In this flammable gas detection apparatus, the concentration of flammable gas can be calculated each time the energization state of the heating resistor is switched to each of the resistance values corresponding to the two set temperatures at regular periods of time. Thus, the gas concentration can be detected accurately and at short intervals.

Effects of the Invention

According to the present invention, a flammable gas detection apparatus in which the decrease in gas concentration detection accuracy accompanying a temporal change in environment temperature is suppressed can be obtained.

MODE FOR CARRYING OUT THE INVENTION

In the following, an embodiment of the present invention will be described with reference to the drawings.

Figure 1:
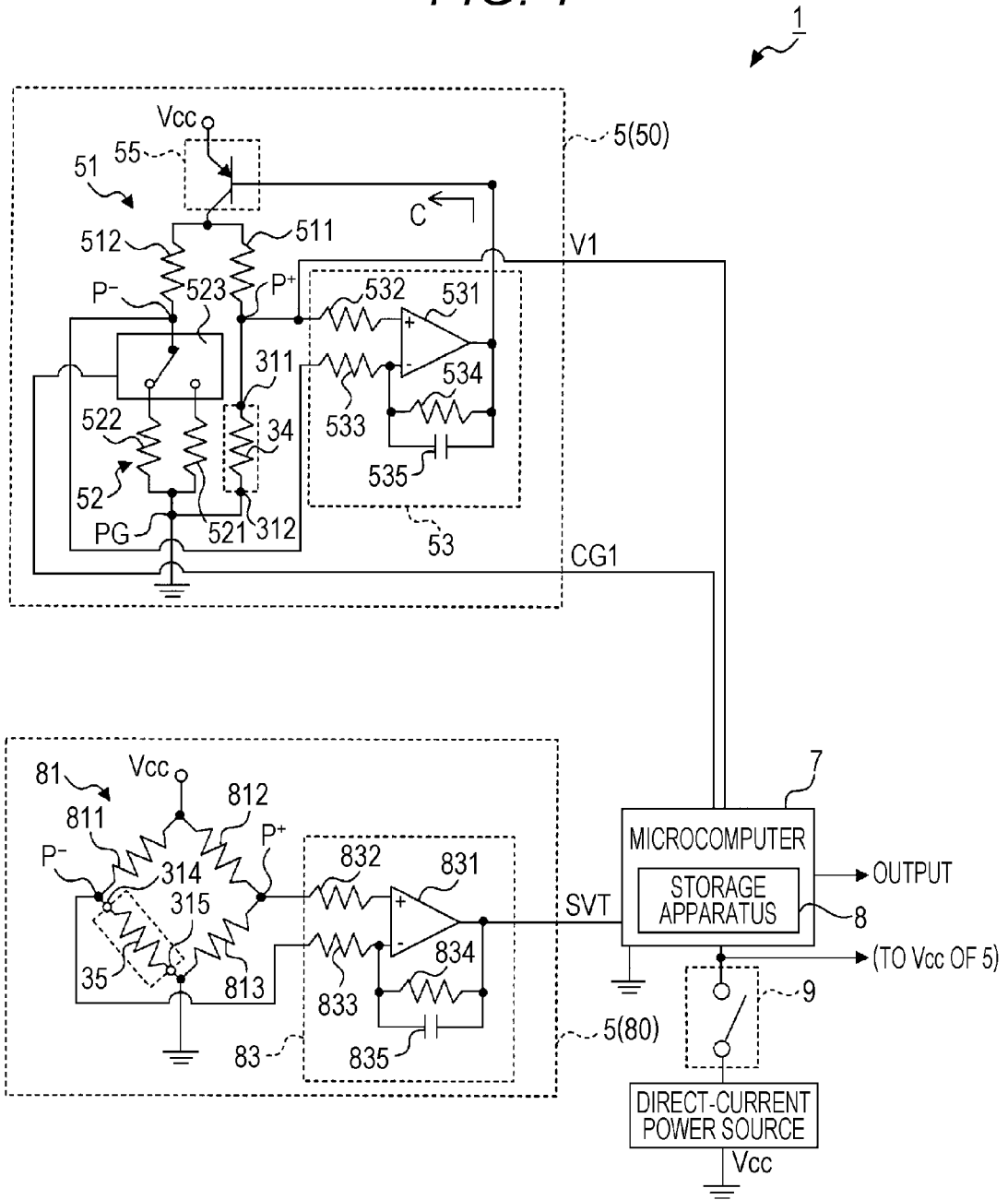
FIG. 1 illustrates an overall configuration of a flammable gas detection apparatus.
Figure 2:
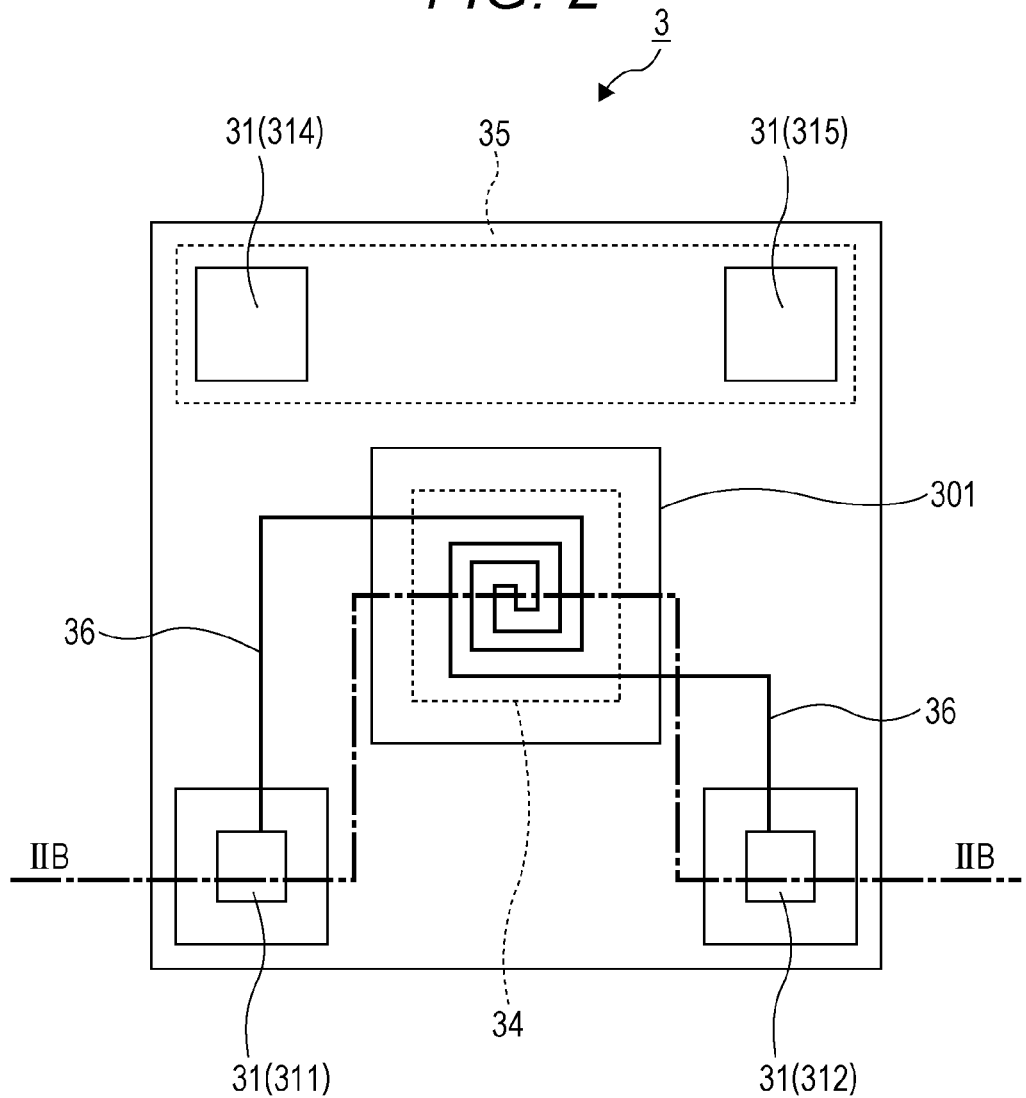
FIG. 2 is a plan view illustrating a configuration of a gas detection element which is a main portion of a flammable gas detection apparatus.
Figure 3:
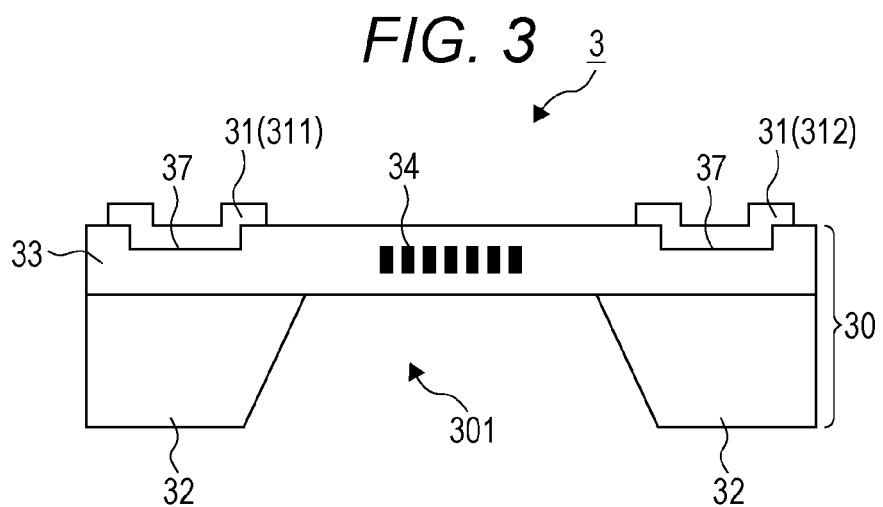
FIG. 3 is a cross-sectional view of the gas detection element taken along line IIB-IIB of FIG. 2.

FIG. 1 illustrates an overall configuration of a flammable gas detection apparatus 1 to which the present invention is applied. FIG. 2 is a plan view of a configuration (part of internal configuration) of a gas detection element 3 which is a main portion of the flammable gas detection apparatus 1. FIG. 3 is a cross-sectional view of the gas detection element taken along line IIB-IIB of FIG. 2.

[Overall Configuration]

The flammable gas detection apparatus 1 detects the concentration of flammable gas by using the gas detection element 3 of heat conduction type. For example, the flammable gas detection apparatus 1 is installed in the cabin of a fuel cell automobile and used for detecting leakage of hydrogen.

As shown in FIG. 1, the flammable gas detection apparatus 1 is provided with a control circuit 5 for drive-controlling the gas detection element 3 (see FIGS. 2 and 3); a microcomputer 7 that produces a change-over signal CG1 for controlling the operation of the control circuit 5 and that performs various processes including a process (gas concentration computation process) of computing the gas concentration of flammable gas contained in gas for detection, based on detection signals V1 and SVT obtained from the control circuit 5; and a start-up switch 9 that starts up or stops the control circuit 5 or the microcomputer 7 by connecting or terminating a power source supply path from a direct-current power source Vcc to the flammable gas detection apparatus 1.

The control circuit 5 (excluding a heating resistor 34 and a temperature-measuring resistor 35 which will be described below), the microcomputer 7, and the start-up switch 9 are formed on a single circuit substrate. The gas detection element 3 is formed separately from the circuit substrate.
[Gas Detection Element]
Next, the gas detection element 3 will be described.

As shown in FIGS. 2 and 3, the gas detection element 3 is provided with a flat-plate shaped (quadrangular in plan view) base portion 30. On one surface of the base portion 30 (hereinafter referred to as "front surface"), a plurality of electrodes 31 is formed. On the other surface (hereinafter referred to as "rear surface"), a recess 301 is formed at around the center of the base portion 30 along one direction of the base portion 30.

The gas detection element 3 is dimensioned on the order of several millimeters both lengthwise and laterally (such as 3 mm×3 mm). The gas detection element 3 is manufactured by micromachining technology (micromachining processing) using a silicon substrate, for example.

The electrodes 31 include two electrodes (electrode pads) 311 and 312 disposed along one side of the base portion 30 (the lower side in FIG. 2) (which will be hereinafter referred to as "first electrode group"), and two electrodes (electrode pads) 314 and 315 disposed along another side (the upper side in FIG. 2) (which will be hereinafter referred to as "second electrode group"). Of these, the electrodes 312 and 315 will be also hereinafter referred to as "ground electrodes". The material of the electrodes 31 is aluminum (Al) or gold (Au), for example.

The base portion 30 includes a silicon substrate 32 and an insulating layer 33 formed on one surface of the substrate 32. The base portion 30 has a diaphragm structure with the recess 301 formed by removing a part of the substrate 32 such that the insulating layer 33 is partly (in a substantially square shape in the present example) exposed. Thus, in the base portion 30, the insulating layer 33 side (with no removal of the substrate 32) is the front surface of the base portion 30, while the substrate 32 side (including the partial removal of the substrate 32) is the rear surface of the base portion 30.

In the insulating layer 33, a spiral-pattern shaped heating resistor 34 is embedded at the portion which is exposed on the rear surface of the base portion 30 by the recess 301. Along a long side (one side) of the base portion 30 on the side where the second electrode group 314, 315 is formed, the temperature-measuring resistor 35 used for temperature measurement is embedded. Thus, the heating resistor 34 is disposed in a region closer to the center than the temperature-measuring resistor 35 in the insulating layer 33, and the temperature-measuring resistor 35 is disposed in the region along one of the four sides forming the edges of the insulating layer 33.

The insulating layer 33 may be formed by a single material or may include a plurality of layers with different materials. As the insulating material of the insulating layer 33, silicon oxide ($SiO_2$) or silicon nitride ($Si_3N_4$) is used, for example.

The heating resistor 34 is made of a conductive material of which the resistance value is changed by a temperature change in the material and which has a large temperature coefficient of resistance. The temperature-measuring resistor 35 is made of a conductive material of which the electric resistance is changed in proportion to temperature (in the present embodiment, the resistance value is increased as the temperature is increased). The heating resistor 34 and the temperature-measuring resistor 35 are both made of the same resistor material, which is platinum (Pt) in the present embodiment.

The heating resistor 34 is connected to the first electrode group 311, 312 via wiring 36 embedded in the same plane as the plane in which the heating resistor 34 is formed, and a wiring film 37. The temperature-measuring resistor 35 is connected to the second electrode group 314, 315 via a wiring film (not shown) embedded in the same plane as the plane in which the temperature-measuring resistor 35 is formed.

As the material of the wiring 36 and the wiring film 37, the same resistor material as for the heating resistor 34 and the temperature-measuring resistor 35 is used. The electrodes 31 formed on the front surface of the base portion 30 and the wiring film 37 formed in the base portion 30 (insulating layer 33) are connected via contact holes (connecting conductor).

Thus, the heating resistor 34 is connected such that one end has continuity with the electrode 311 while the other end has continuity with the ground electrodes 312. The temperature-measuring resistor 35 is connected such that one end has continuity with the electrodes 314 and the other end has continuity with the ground electrodes 315.
[Control Circuit]
Next, a configuration of the control circuit 5 will be described.

As shown in FIG. 1, the control circuit 5 is provided with an energization control circuit 50 that controls energization of the heating resistor 34 and that outputs a detection signal V1 corresponding to a voltage across the heating resistor 34; and a temperature adjustment circuit 80 that energizes the temperature-measuring resistor 35 and that outputs a temperature detection signal SVT indicating the temperature of the atmosphere for detection.
[Energization Control Circuit]
The energization control circuit 50 is provided with a bridge circuit (Wheatstone bridge circuit) 51 including the heating resistor 34; an amplification circuit 53 that amplifies a potential difference detected by the bridge circuit 51; and a current adjustment circuit 55 that increases or decreases a current that flows through the bridge circuit 51 in accordance with the output from the amplification circuit 53.

The current adjustment circuit 55 is provided with a transistor connected to a power source line supplying direct-current power source Vcc to the bridge circuit 51, the energization state (on-resistance) of the transistor changing in accordance with the output from the amplification circuit 53, i.e., an adjustment signal C. Specifically, the current adjustment circuit 55 is configured such that as the adjustment signal C is increased, the on-resistance is increased and the current that flows through the bridge circuit 51 is decreased, and, conversely, as the adjustment signal is decreased, the on-resistance is decreased and the current that flows through the bridge circuit 51 is increased.

The amplification circuit 53 is provided with an operational amplifier 531; fixed resistors 532 and 533 connected to an inverting input terminal and a non-inverting input terminal, respectively, of the operational amplifier 531; and a known differential amplification circuit including a fixed resistor 534 and a capacitor 535 which are connected in parallel between the inverting input terminal and the output terminal of the operational amplifier 531.

The amplification circuit 53 is configured such that, when the input voltage at the non-inverting input terminal is greater than the input voltage at the inverting input terminal, the output of the amplification circuit 53, i.e., the adjustment signal C, is increased (and therefore the current that flows through the bridge circuit 51 is decreased). Conversely, when the input voltage at the non-inverting input terminal is smaller than the input voltage at the inverting input terminal, the adjustment signal C becomes smaller (and therefore the current that flows through the bridge circuit 51 is increased).

The bridge circuit 51 is provided with the heating resistor 34; two fixed resistors 511 and 512; and a variable resistor unit 52 with switchable resistance value. The fixed resistor 511 and the heating resistor 34 are connected in series, and the fixed resistor 512 and the variable resistor unit 52 are connected in series. Of each of the series circuits, the end portion PG on the heating resistor 34 or variable resistor unit 52 side is grounded, while the end portion on the fixed resistors 511 and 512 side is connected to the power source side (current adjustment circuit 55).

A connection point P+ of the fixed resistor 511 and the heating resistor 34 is connected to the non-inverting input terminal of the operational amplifier 531 via the fixed resistor 532. A connection point P− of the fixed resistor 512 and the variable resistor unit 52 is connected to the inverting input terminal of the operational amplifier 531 via the fixed resistor 533. Further, the potential at the connection point P+ is supplied to the microcomputer 7 as the detection signal V1.

The variable resistor unit 52 is provided with two fixed resistors 521 and 522 with different resistance values, and a change-over switch 523 for causing one of the fixed resistors 521 and 522 to be effectively operated in accordance with the change-over signal CG1 from the microcomputer 7. By switching the resistance value of the variable resistor unit 52 by the change-over switch 523, the balance of the bridge circuit 51 can be changed.

The fixed resistor 521 has a resistance value such that the heating resistor 34 has a first set temperature CH (such as 400° C.). The fixed resistor 522 has a resistance value such that the heating resistor 34 has a second set temperature CL (such as 300° C.) which is set to be lower than the first set temperature CH.

In the energization control circuit 50 of the above configuration, as energization of the bridge circuit 51 from the direct-current power source Vcc is started, the amplification circuit 53 and the current adjustment circuit 55 adjust the current that flows through the bridge circuit 51 such that the potential difference between the connection points P+ and P− becomes zero. Thus, the resistance value (and therefore temperature) of the heating resistor 34 is controlled to a constant value (and therefore the first set temperature CH or the second set temperature CL) determined by the variable resistor unit 52.

Specifically, when the amount of the flammable gas contained in the atmosphere for detection is changed and the amount of heat generated by the heating resistor 34 is exceeded by the amount of heat taken away by the flammable gas, the temperature of the heating resistor 34 is decreased, whereby the resistance value of the heating resistor 34 is decreased. Conversely, when the amount of heat generated by the heating resistor is greater than the amount of heat taken away by the flammable gas, the temperature of the heating resistor 34 is increased, so that the resistance value of the heating resistor 34 is increased.

On the other hand, when the resistance value of the heating resistor 34 is decreased, the amplification circuit 53 and the current adjustment circuit 55 increase the current that flows through the bridge circuit 51 and therefore the amount of heat generated by the heating resistor 34. Conversely, when the resistance value of the heating resistor 34 is increased, the amplification circuit 53 and the current adjustment circuit 55 decrease the current that flows through the bridge circuit 51 and therefore the amount of heat generated by the heating resistor 34. In this way, the resistance value (and therefore temperature) of the heating resistor 34 is maintained at a constant value.

Namely, the detection signal V1 representing the potential at the connection point P+ indicates the magnitude of the current that flows through the heating resistor 34, i.e., the amount of heat required to maintain a certain temperature (resistance value) of the heating resistor 34 (and hence the amount of heat taken away by the flammable gas). Because the amount of heat reflects the gas concentration, the gas concentration of flammable gas can be learned from the detection signal V1. More specifically, during the calculation of the gas concentration, humidity H in the atmosphere for detection is used for correction, as will be described later with reference to a gas concentration computation process.

[Temperature Measurement Circuit]

The temperature adjustment circuit 80 is provided with a bridge circuit (Wheatstone bridge) 81 including the temperature-measuring resistor 35, and an amplification circuit 83 that amplifies the potential difference obtained from the bridge circuit 81.

The amplification circuit 83 is provided with an operational amplifier 831; fixed resistors 832 and 833 connected to the inverting input terminal and the non-inverting input terminal, respectively, of the operational amplifier 831; and a known differential amplification circuit including a fixed resistor 834 and a capacitor 835 which are connected in parallel between the inverting input terminal and the output terminal of the operational amplifier 831.

The bridge circuit 81 is provided with the temperature-measuring resistor 35 and three fixed resistors 811, 812, and 813. The fixed resistor 811 and the temperature-measuring resistor 35 are connected in series. The fixed resistor 812 and the fixed resistor 813 are connected in series. Of each of the series circuits, the end portion on the temperature-measuring resistor 35 and fixed resistor 813 side is grounded, while the end portion on the fixed resistors 811 and 812 side is connected to power source.

A connection point P− of the fixed resistor 811 and the temperature-measuring resistor 35 is connected to the inverting input terminal of the operational amplifier 531 via the fixed resistor 833. A connection point P+ of the fixed resistor 812 and the fixed resistor 813 is connected to the non-inverting input terminal of the operational amplifier 831 via the fixed resistor 832. The output of the operational amplifier 831 is supplied to the microcomputer as the temperature detection signal SVT.

The temperature-measuring resistor 35 is set such that the temperature detection signal SVT has a reference value when the temperature of the atmosphere for detection to which the gas detection element 3 is exposed is at a preset reference temperature.

As the temperature of the atmosphere for detection is changed, the resistance value of the temperature-measuring resistor 35 is changed and a potential difference is produced. The potential difference is amplified and outputted as the temperature detection signal SVT.

Regarding the connection of the gas detection element 3 and the control circuit 5, the electrodes 31 (311, 312, 314, 315) of the gas detection element 3 are connected such that the electrode 311 is connected to the connection point P+ of the energization control circuit 50, the electrode 314 is connected to the connection point P− of the temperature adjustment circuit 80, and the ground electrodes 312 and 315 are connected to the common ground line of the control circuit 5.

[Microcomputer]

The microcomputer 7 is a known one provided with a storage apparatus 8 (such as ROM and RAM) for storing various programs or data for performing the gas concentration computation process and the like; a CPU for executing the programs stored in the storage apparatus 8; an IO port for the input and output of various signals; and a counting timer, for example.

The signal level of the detection signal V1 that is detected at the first set temperature CH (400° C.) will be referred to as a high temperature voltage VH. The signal level of the detection signal V1 that is detected at the second set temperature CL (300° C.) will be referred to as a low temperature voltage VL. The signal level of the temperature detection signal SVT that is read from the temperature adjustment circuit 80 will be referred to as a temperature voltage VT.

The data stored in the storage apparatus 8 include at least temperature conversion data representing the correlation between the environment temperature T in the atmosphere for detection and the temperature voltage VT; humidity conversion data representing the correlation between the humidity H in the atmosphere for detection, the high temperature voltage VH, the low temperature voltage VL, and the temperature voltage VT; and concentration conversion data representing the correlation between the high temperature voltage VH or the low temperature voltage VL (according to the present embodiment, the high temperature voltage VH is used) and the gas concentration X of the flammable gas. Specifically, the respective conversion data include conversion map data, calculation formulae for conversion, and the like, and are prepared in advance based on experimentally obtained data, for example.

The humidity conversion data include voltage ratio conversion map data representing the correlation between the environment temperature T (and therefore temperature voltage VT) and a voltage ratio VC(0) which will be described later; and humidity conversion map data representing the correlation between a voltage ratio difference ΔVC which will be described later and the humidity H. Further, the concentration conversion data include high temperature voltage conversion map data representing the correlation between the temperature voltage VT and a high temperature voltage VH(0) which will be described later; humidity/voltage change conversion map data representing the correlation between the high temperature voltage VH and the humidity H and a high temperature voltage change ΔVH(H) which will be described later; and gas sensitivity conversion map data representing the correlation between the temperature voltage VT and the high temperature voltage VH and a gas sensitivity G(VT) which will be described later.

The microcomputer 7 is started up in response to the start of feeding of electricity from the direct-current power source Vcc when the start-up switch 9 is turned on. After the various units of the microcomputer 7 are initialized, the microcomputer 7 starts the gas concentration computation process.

The energization control circuit 50 and the microcomputer 7 that outputs the change-over signal CG1 correspond to an example of the energization control unit. The microcomputer 7 that performs the gas concentration computation process corresponds to an example of the gas concentration computation unit.

[Gas Concentration Computation Process According to First Embodiment]

Figure 4:
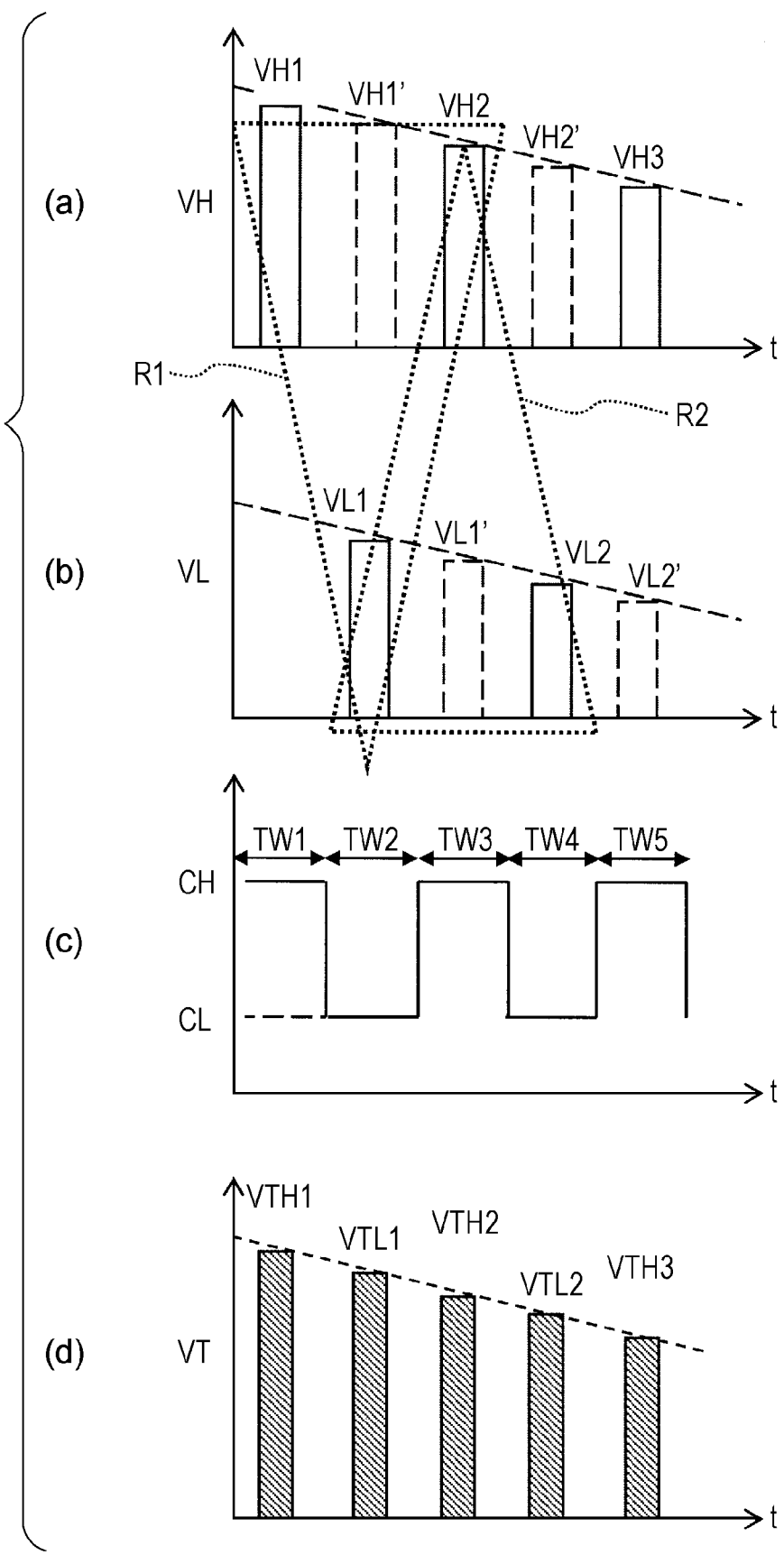
FIG. 4 shows time charts of the timing of acquisition of VH and VL, a time chart of the first set temperature (CH) and the second set temperature (CL) of the heating resistor, and a time chart of the timing of acquisition of the temperature of a temperature-measuring resistor according to a first embodiment.
Figure 5:
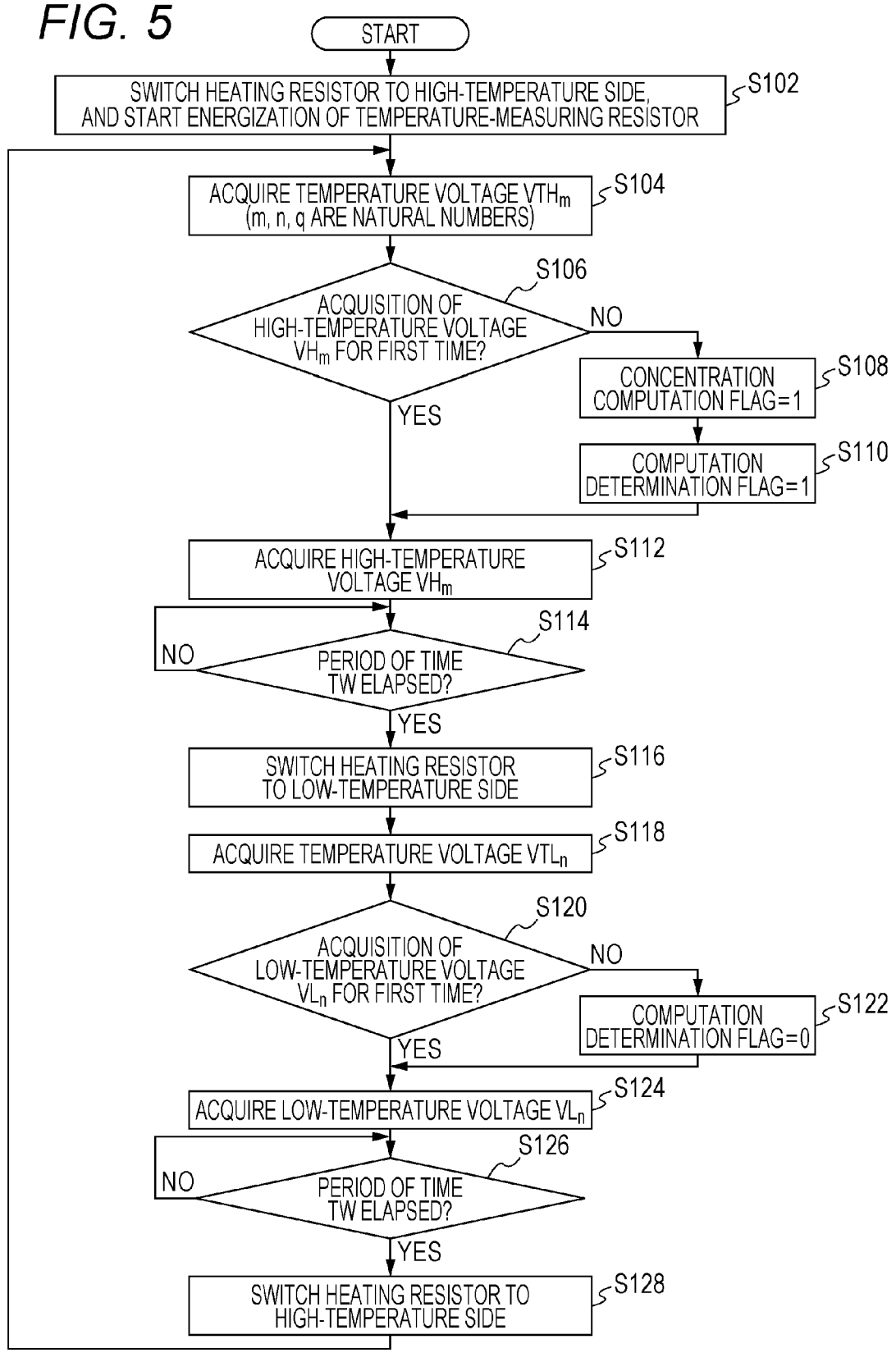
FIG. 5 is a flowchart of a process for acquiring VH, VL, and VT according to the first embodiment.
Figure 6:
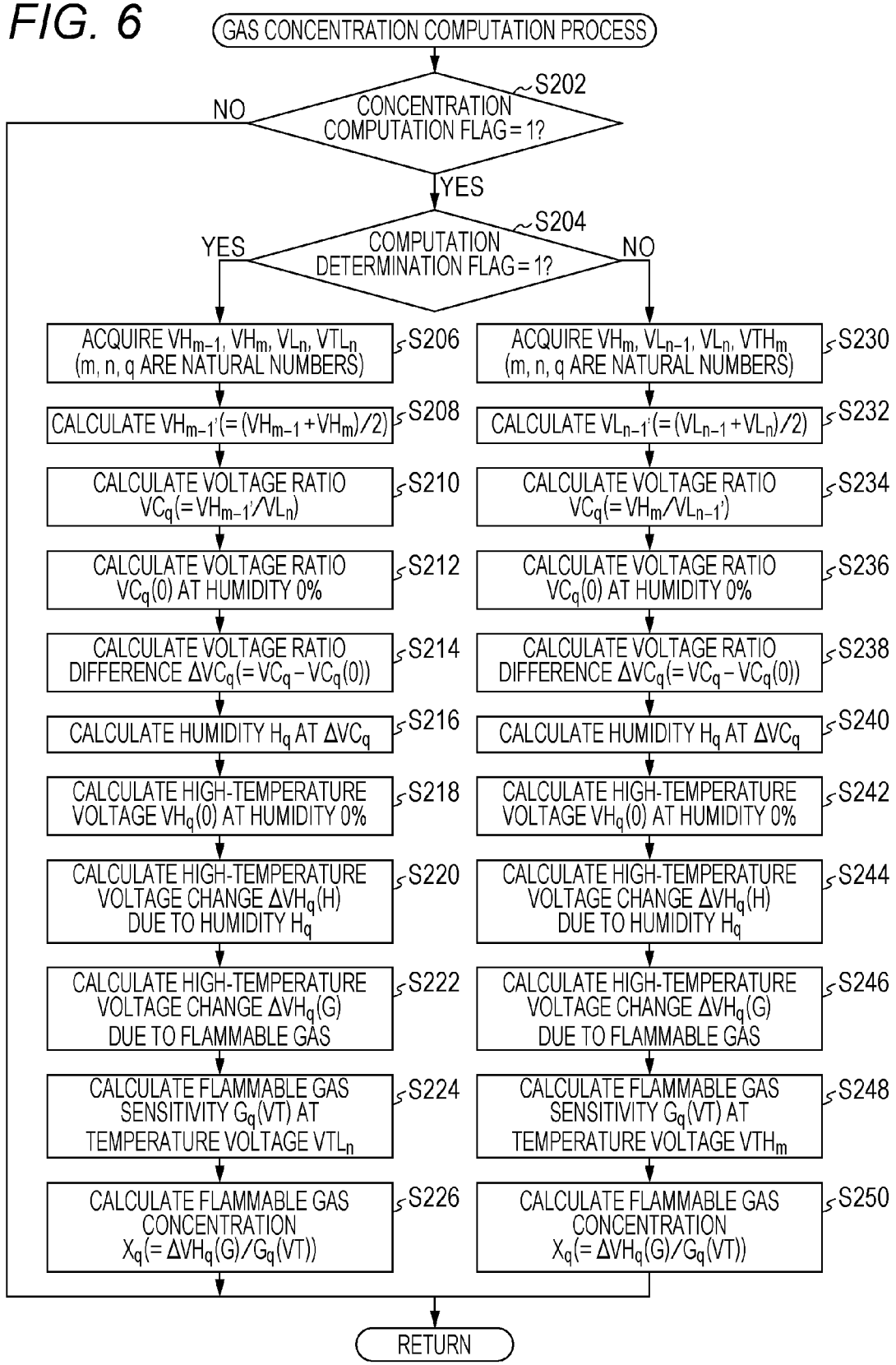
FIG. 6 is a flowchart of a gas concentration computation process using an average high temperature voltage VH' and an average low temperature voltage VL' according to the first embodiment.

With reference to FIGS. 4 to 6, the gas concentration computation process in the flammable gas detection apparatus according to the first embodiment of the present invention will be described. FIG. 4 shows time charts indicating the timing for acquiring VH and VL (FIGS. 4(a), (b)); a time chart indicating the first set temperature (CH) and the second set temperature (CL) of the heating resistor (FIG. 4(c)); and a time chart indicating the timing of acquiring the temperature (temperature voltage VT) of the temperature-measuring resistor (FIG. 4(d)). FIG. 5 is a flowchart of a process for acquiring VH, VL, and VT. FIG. 6 is a flowchart of the gas concentration computation process using an average high temperature voltage VH' and an average low temperature voltage VL', which will be described later.

As shown in FIG. 4, when the environment temperature is increased during detection, VH and VL are decreased over time (FIG. 4(a), (b)). Thus, when, VH1 is detected in the initial period of time TW1 and then VL1 is detected in the next period of time TW2, the value of the low temperature voltage becomes smaller than if detected at the same timing (period of time TW1) as for VH1. Accordingly, in the first embodiment, gas concentration is computed based on the relationship (which is referred to as "first information group") between the average high temperature voltage VH1' which is an average of the two temporally successive values of VH1 and VH2 in the periods of time TW1 and TW3, and VL1 in the period of time TW2 between VH1 and VH2. The VHs and VL used in the first information group are indicated by an inverted triangular region R1 in FIG. 4.

Thus, a predicted value (average high temperature voltage VH1') of the high temperature voltage at the same detection timing (period of time TW2) as for the low temperature voltage (VL1) is estimated from the high temperature voltages (VH1, VH2) in the other periods of time TW1 and TW3. Accordingly, the voltage difference and voltage ratio of VH and VL can be obtained at the same detection timing, so that the decrease in gas concentration detection accuracy accompanying a temporal change in environment temperature can be suppressed. By using the environment temperature in the period of time TW2 (temperature voltage VTL1) in the first information group, the environment temperature at the same detection timing as the timing of calculation of the voltage difference and voltage ratio of VH and VL (the first information group) can be used for the computation of gas concentration. Namely, in the gas concentration computation process according to the first embodiment, gas concentration is computed based on the first information group including the average high temperature voltage VH1' which is an average of the values of the two temporally successive high temperature voltages VH1 and VH2; the low temperature voltage VL1 in the period of time TW2 between the two high temperature voltages VH1 and VH2; and the environment temperature VTL1 in the period of time TW2 in which the low temperature voltage VL1 is detected.

In FIG. 4, the high temperature voltage is detected in the order of the suffix 1, 2, and 3 of the high temperature voltage (VH) chronologically. Similarly, the low temperature voltage is detected in the order of the suffix 1, 2, and 3 of the low temperature voltage (VL) chronologically. The temperature voltage VTL represents the temperature voltage (VT) in the same period of time as when the low temperature voltage (VL) is detected. The temperature voltage VTH represents the temperature voltage (VT) in the same period of time as when the high temperature voltage (VH) is detected.

Further, according to the first embodiment, after the first information group is calculated in the period of time TW3 as described above, the low temperature voltage VL1 used for calculating the first information group and the low temperature voltage VL2 detected in the next period of time TW4 are averaged to calculate an average low temperature voltage VL1'. Then, gas concentration is computed based on the relationship (which is referred to as "second information group") between VL1' and VH2 in the period of time TW3 between VL1 and VL2. The VH and VL used for the second information group are indicated by a triangular region R2 in FIG. 4.

Also, in the second information group, the predicted value (average low temperature voltage VL1') of the low temperature voltage in the same detection timing (period of time TW3) as for the high temperature voltage (VH2) is estimated from the low temperature voltages (VL1, VL2) in the other periods of time TW2 and TW4. Thus, the voltage difference and voltage ratio of VH and VL can be obtained at the same detection timing, so that the decrease in gas concentration detection accuracy accompanying a temporal change in environment temperature can be suppressed. By using the environment temperature (temperature voltage VTH2) in the period of time TW3 in the second information group, the environment temperature in the same detection timing as the timing of calculation of the voltage difference and voltage ratio of VH and VL (the second information group) can be used for computing gas concentration. Thus, in the gas concentration computation process according to the first embodiment, gas concentration is also computed based on the second information group including the average high temperature voltage VL1' averaging the values of the two temporally successive low temperature voltages VL1 and VL2; the high temperature voltage VH2 in the period of time TW3 between the two low temperature voltages VL1 and VL2; and the environment temperature VTH2 in the period of time TW3 in which the high temperature voltage VH2 is detected.

After the second information group is calculated in the period of time TW4 as described above, the first information group is calculated in the same way as described above by using the high temperature voltage VH2 used for calculating the second information group, and the high temperature voltage VH3 which is detected in the next period of time TW5. By thus calculating the first information group and the second information group alternately, the voltage difference and voltage ratio of VH and VL (the first information group and the second information group) can be obtained at the same detection timing in each period of time TW4, TW5, and so on, following the period of time TW3. Accordingly, gas concentration detection accuracy can be further increased. In contrast, when only one of the first information group and the second information group is calculated, as according to the second embodiment which will be described later, the calculation timing becomes twice the period of time (see FIG. 7).

Next, with reference to FIGS. 5 and 6, a process performed by the CPU of the microcomputer 7 for acquiring VH, VL, and VT, and the gas concentration computation process will be described. Regarding the computation of the gas concentration X, a method exists by which the gas concentration X is determined from the low temperature voltage VL or the high temperature voltage VH by using concentration conversion data, and further the environment temperature T is determined from the temperature voltage VT by using temperature conversion data. In this method, the gas concentration X as a computation result is corrected by using only the environment temperature T, which is also a computation result. Herein, however, the gas concentration X is determined by using the humidity H in addition to the environment temperature T. In this case, the humidity H is calculated by using the voltage ratio of VH and VL at the same detection timing, as will be described later.

As shown in FIG. 5, in the process for acquiring VH, VL, and VT, first in step S102, the CPU switches the heating resistor 34 to the high temperature side (the first set temperature (CH) side), and starts energizing the temperature-measuring resistor 35. Specifically, the CPU implements a process for maintaining the resistance value of the bridge circuit 51, i.e., the set temperature of the heating resistor 34, at the first set temperature CH during the regular period of time TW by using the change-over signal CG1.

Then, in S104, the CPU acquires the temperature voltage VTHm in the period of time of S102. FIG. 4(c) is a time chart indicating the temperature of the heating resistor, and FIG. 4(d) is a time chart indicating the timing of acquiring the temperature voltage VT. The suffix m, the suffix n which will be described later, and the suffix q which will be described later are natural numbers, indicating that the voltage is chronologically acquired in the order of 1, 2, and 3 (the same applies in the following).

Next, in S106, the CPU determines whether the high temperature voltage (VHm) is acquired for the first time, i.e., whether it is VH1. If "No", the CPU allocates "1" to the concentration computation flag (S108), and allocates "1" to the computation determination flag (S110), and the process advances from S110 to S112. On the other hand, if it is "Yes" in S106, the process directly moves to S112.

The concentration computation flag-1 means that VHm has been acquired for a plurality of times, and indicates that, as described with reference to FIG. 4, the two values of the successive VHm-1 and VHm can be averaged to calculate an average high temperature voltage VHm-1'. The computation determination flag is a flag for determining whether the average high temperature voltage VHm-1' or the average low temperature voltage VLn-1' should be calculated in the flow of FIG. 6 which will be described later. When the computation determination flag=1, a process for calculating the average high temperature voltage VHm-1' is performed.

Then, in S112, the CPU acquires the high temperature voltage (VHm) of the heating resistor 34 and determines whether the period of time TW has elapsed (S114). If "Yes" in S114, the process advances to S116; if "No", the process returns to S114 and waits for the elapse of the period of time TW. In the example of FIGS. 5 and 6, TW=200 msec.

Then, in S116, the CPU switches the heating resistor 34 to the low temperature side (the second set temperature (CL) side), and acquires the temperature voltage VTLn in the period of time of S116 (S118).

Then, in S120, the CPU determines whether the acquisition of the low temperature voltage (VLn) is for the first time, i.e., whether it is VL1 or not. If "Yes", the process moves to S124; if "No", the CPU allocates "0" to the computation determination flag (S122). When the computation determination flag-0, as described with reference to FIG. 4, the values of successive two VLn-1 and VLn can be averaged to calculate the average low temperature voltage VLn-1'. Thus, the process for calculating the average low temperature voltage VLn-1' is performed. After S122, the process moves to S124.

Then, in S124, the CPU acquires the low temperature voltage (VLn) of the heating resistor 34 and determines whether the period of time TW has elapsed (S126). If "Yes" in S126, the process moves to S128; if "No", the process returns to S126 and waits for the elapse of the period of time TW.

In S128, the CPU switches the heating resistor 34 to the high temperature side (the first set temperature (CH) side), and returns to S104.

The VHm, VLn, VTHm, and VTLn that are acquired as described above are stored in the storage apparatus 8 (RAM) in association with the concentration computation flag and the computation determination flag, and are read in the following gas concentration computation process.

With reference to FIG. 6, the gas concentration computation process will be described. The gas concentration computation process is performed in each period of time TW. Namely, because the interval of S104 to S114 in FIG. 5 is processed in the period of time TW, the gas concentration computation process in which the computation determination flag of S110 is read is performed upon the elapse of S114. Further, the interval of S116 to S126 is processed in the next period of time TW, and the next gas concentration computation process in which the computation determination flag of S122 is read is performed upon the elapse of S126.

In FIG. 6, first, in step S202, the CPU determines whether the concentration computation flag is "1". If "Yes" in S202, the process moves to S204; if "No", the present gas concentration computation process is terminated and prepares for the next time. Then, in S204, the CPU determines whether the computation determination flag is "1". If "Yes" in S204 (i.e., when the process for acquiring the two temporally successive high temperature voltages VHm-1 and VHm has been performed in S104 to S114 in FIG. 5), the process moves to S206, where VHm-1, VHm, and VLn are acquired from the energization control circuit 50 and VTLn is acquired from the temperature adjustment circuit 80. Here, the case of m=2 and n=1 corresponds to R1 in FIG. 4, so that the gas concentration computation process is one that is based on the first information group including the average high temperature voltage VHm-1', the low temperature voltage VLn, and the temperature voltage VTLn in the period of time in which the low temperature voltage VLn is acquired. On the other hand, if "No" in S204, the process advances to the gas concentration computation process based on the second information group including the average low temperature voltage VLn-1', the high temperature voltage VHm, and the temperature voltage VTHm in the period of time in which the high temperature voltage VHm is acquired.

Next, in S208, the CPU calculates the average high temperature voltage VHm-1'. Specifically, the VHm-1' is calculated by using VHm-1 and VHm acquired in S206 as input values for the following expression (1):

$$VHm-1' = (VHm-1 + VHm)/2 \tag{1}$$

Then, in S210, the CPU calculates the voltage ratio VCq by using VLn acquired in S206 and VHm-1' calculated in S208 as input values for the following expression (2):

$$VCq = VHm-1'/VLn \tag{2}$$

Then, in S212, based on the temperature voltage VTLn acquired in S206 and the voltage ratio conversion map data, the voltage ratio VCq(0) in the case where the gas concentration X and the humidity H at the environment temperature TLn (and therefore temperature voltage VTLn) are zero is calculated.

In S214, using the voltage ratio VCq calculated in S210 and the VCq(0) calculated in S212 as the input values for the following expression (3), the voltage ratio difference ΔVCq at the environment temperature TLn (and therefore temperature voltage VTLn) is calculated.

$$\Delta VCq = VCq - VCq(0) \tag{3}$$

Then, in S216, based on the voltage ratio difference ΔVCq calculated in S214 and the humidity conversion map data, the humidity Hq at the voltage ratio difference ΔVCq is calculated.

Then, in S218, based on the VHm-1' calculated in S208, the VTLn acquired in S206, and the high temperature voltage conversion map data, the high temperature voltage VHq(0) in the case where the gas concentration X and the humidity H at the environment temperature TLn (and therefore temperature voltage VTLn) are zero is calculated.

Then, in S220, based on the VHm-1' calculated in S208, the humidity Hq calculated in S216, and the humidity/voltage change conversion map data, the high temperature voltage change ΔVHq(H) representing a voltage change portion of VHm-1' which is due to the humidity Hq is calculated.

Then, in S222, using the VHm-1' calculated in S208, the VHq(0) calculated in S218, and the ΔVHq(H) calculated in S220 as input values for the following expression (4), the high temperature voltage change ΔVHq(G) representing a voltage change portion of VHm-1' which is due to flammable gas is calculated.

$$\Delta VHq(G) = VHm-1' - VHq(0) - \Delta VHq(H) \tag{4}$$

Then, in S224, based on the VHm-1' calculated in S208, the VTLn calculated in S206, and the gas sensitivity conversion map data, the gas sensitivity Gq(VT) representing the sensitivity (of which the unit is the inverse of the gas concentration X) of VHm-1' with respect to a flammable gas which is pre-set for each environment temperature TLn (and therefore temperature voltage VTLn) is calculated.

Finally, in S226, using the high temperature voltage change ΔVHq(G) calculated in S222 and the gas sensitivity Gq(VT) calculated in S224 as input values for the following expression (5), the gas concentration Xq of flammable gas is calculated, and the present gas concentration computation process is completed.

$$Xq = \Delta VHq(G)/Gq(VT) \tag{5}$$

On the other hand, when "No" in S204 (namely, when the process for acquiring the two temporally successive low temperature voltages VLn-1 and VLn has been performed in S116 to S126 in FIG. 5), the process moves to S230, and VLn-1, VLn, and VHm are acquired from the energization control circuit 50 and VTHm is acquired from the temperature adjustment circuit 80. The case where m=2 and n=2 corresponds to R2 in FIG. 4.

Then, in S232, the CPU calculates the average low temperature voltage VLn-1'. Specifically, using the VLn-1 and VLn acquired in S230 as input values for the following expression (6), VLn+1' is calculated:

$$VLn-1' = (VLn-1 + VLn)/2 \tag{6}$$

Then, in S234, the CPU calculates the voltage ratio VCq by using the VHm acquired in S230 and the VLn-1' calculated in S232 as input values for the following expression (7):

$$VCq = VHm/VLn-1' \tag{7}$$

While the suffix q is a natural number that increases in chronological order, it is not a value directly linked with m or n. Thus, the suffix is denoted as "q" throughout instead of as "q+1" and the like. For example, when VC1(q=1) in the process following S206 and the determination in S204 is "NO", VC2(q=2) in the process following S230 and the suffix is incremented by one after each calculation.

Then, in S236, based on the temperature voltage VTHm acquired in S230 and the voltage ratio conversion map data, the voltage ratio VCq(0) in the case where the gas concentration X and the humidity H at the environment temperature THm (and therefore temperature voltage VTHm) are zero is calculated.

Then, in S238, using the voltage ratio VCq calculated in S234 and the VCq(0) calculated in S236 as input values for the following expression (8), the voltage ratio difference ΔVCq at the environment temperature THm (and therefore temperature voltage VTHm) is calculated.

$$\Delta VCq = VCq - VCq(0) \tag{8}$$

Then, in S240, based on the voltage ratio difference ΔVCq calculated in S238 and the humidity conversion map data, the humidity Hq at the voltage ratio difference ΔVCq is calculated.

Then, in S242, based on the VLn-1' calculated in S232, the VTHm acquired in S230, and the high temperature voltage conversion map data, the high temperature voltage VHq(0) in the case where the gas concentration X and the humidity H at the environment temperature THm (and therefore temperature voltage VTHm) are zero is calculated.

Thereafter, in S244, based on the VHm acquired in S230, the humidity Hq calculated in S240, and the humidity/voltage change conversion map data, the high temperature voltage change ΔVHq(H) representing a voltage change portion of VHm which is due to the humidity Hq is calculated.

Then, in S246, using the VHm acquired in S230, the VHq(0) calculated in S242, and the ΔVHq(H) calculated in S244 as input values for the following expression (9), the high temperature voltage change ΔVHq(G) representing a voltage change portion of VHm which is due to the flammable gas is calculated.

$$\Delta VHq(G) = VHm - VHq(0) - \Delta VHq(H) \quad (9)$$

Thereafter, in S248, based on the VHm acquired in S230, the VTHq acquired in S230, and the gas sensitivity conversion map data, the gas sensitivity Gq(VT) representing the sensitivity (of which the unit is the inverse of the gas concentration X) of VHm with respect to a flammable gas which is pre-set for each environment temperature THm (and therefore temperature voltage VTHm) is calculated.

Finally, in S250, using the high temperature voltage change ΔVHq(G) calculated in S246 and the gas sensitivity Gq(VT) calculated in S248 as input values for the following expression (10), the gas concentration Xq of flammable gas is calculated, and then the process returns to the start of the gas concentration computation process.

$$Xq = \Delta VHq(G)/Gq(VT) \quad (10)$$

Thus, in the processes of FIGS. 5 and 6, the change-over signal CG1 is outputted to the change-over switch 523 in each period of time TW so as to switch the energization path (in the variable resistor unit 52) between the connection point P− of the fixed resistor 512 and the variable resistor unit 52 and the end portion PG (the ground-side end portion of the variable resistor unit 52) from one of the fixed resistors 521 and 522 to the other, whereby the high temperature voltages VHm-1 and VHm, the low temperature voltages VLn-1 and VLn, and the temperature voltages VTLn and VTHm are acquired. Then, in the gas concentration computation process, the environment temperatures TLn and THm are computed based on the temperature voltages VTLn and VTHm, respectively.

Further, the predicted value (average high temperature voltage VHm-1') of the high temperature voltage in the same detection timing (period of time) as the low temperature voltage VLn is estimated from the high temperature voltages (VHm-1, VHm) in other periods of time, the humidity Hq in the atmosphere for detection is computed from the voltage ratio of the high temperature voltage VHm-1' and the low temperature voltage VLn, and the gas concentration Xq is corrected by using the environment temperature TLn and the humidity Hq. Similarly, the predicted value (average low temperature voltage VLn-1') of the low temperature voltage in the same detection timing (period of time) as the high temperature voltage VHm is estimated from the low temperature voltages (VLn-1, VLn) in other periods of time, the humidity Hq in the atmosphere for detection is computed from the voltage ratio of the high temperature voltage VHm and the low temperature voltage VLn-1', and the gas concentration Xq is corrected by using the environment temperature THm and the humidity Hq.

Thus, the voltage ratio at the same detection timing can be obtained, so that the decrease in gas concentration detection accuracy accompanying a temporal change in environment temperature can be suppressed.

[Gas Concentration Computation Process in Second Embodiment]

Figure 7:
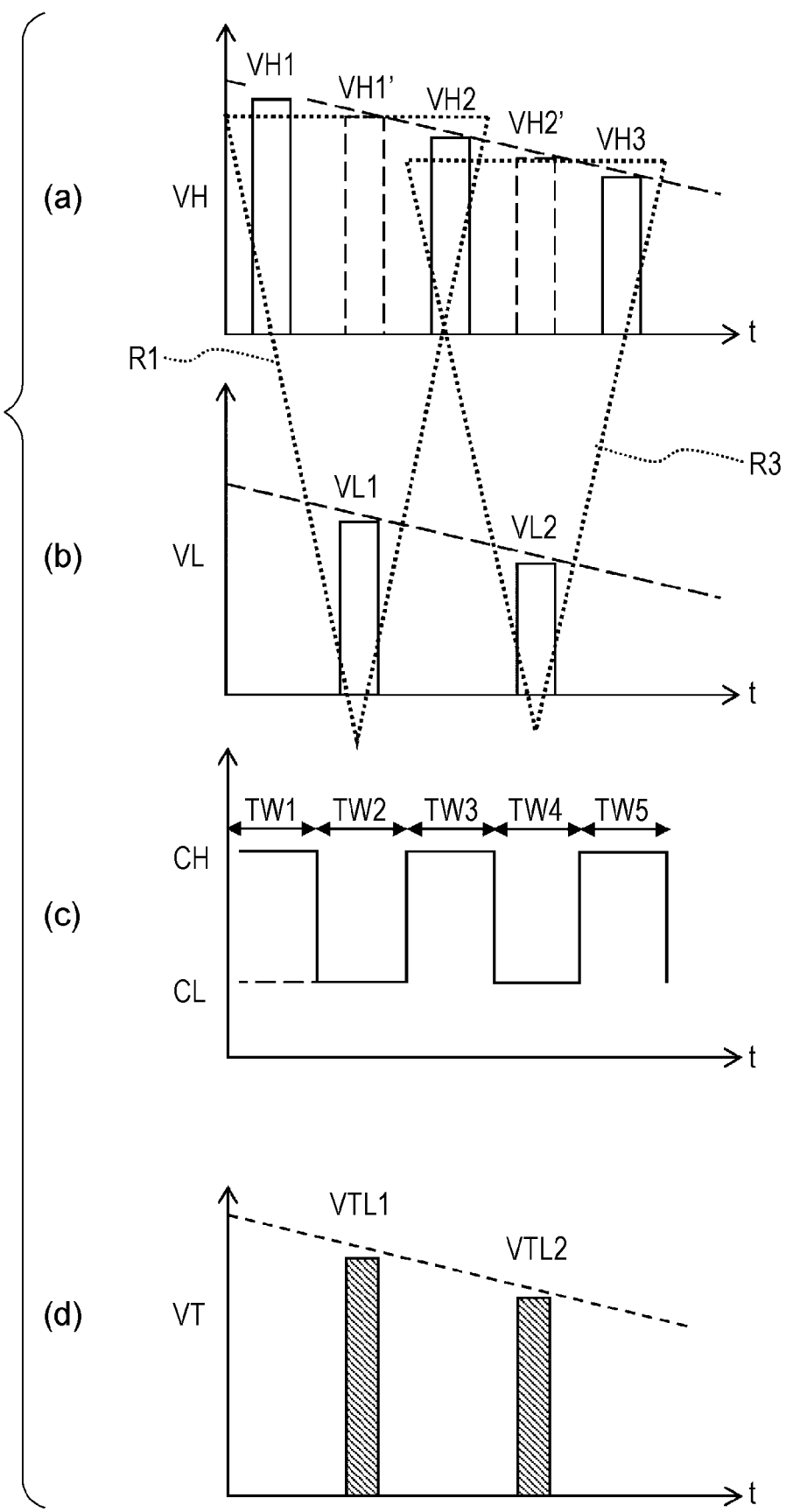
FIG. 7 shows time charts of the timing for acquiring VH and VL according to a second embodiment, a time chart of the first set temperature (CH) and the second set temperature (CL) of the heating resistor, and a time chart of the timing for acquiring the temperature of the temperature-measuring resistor.
Figure 8:
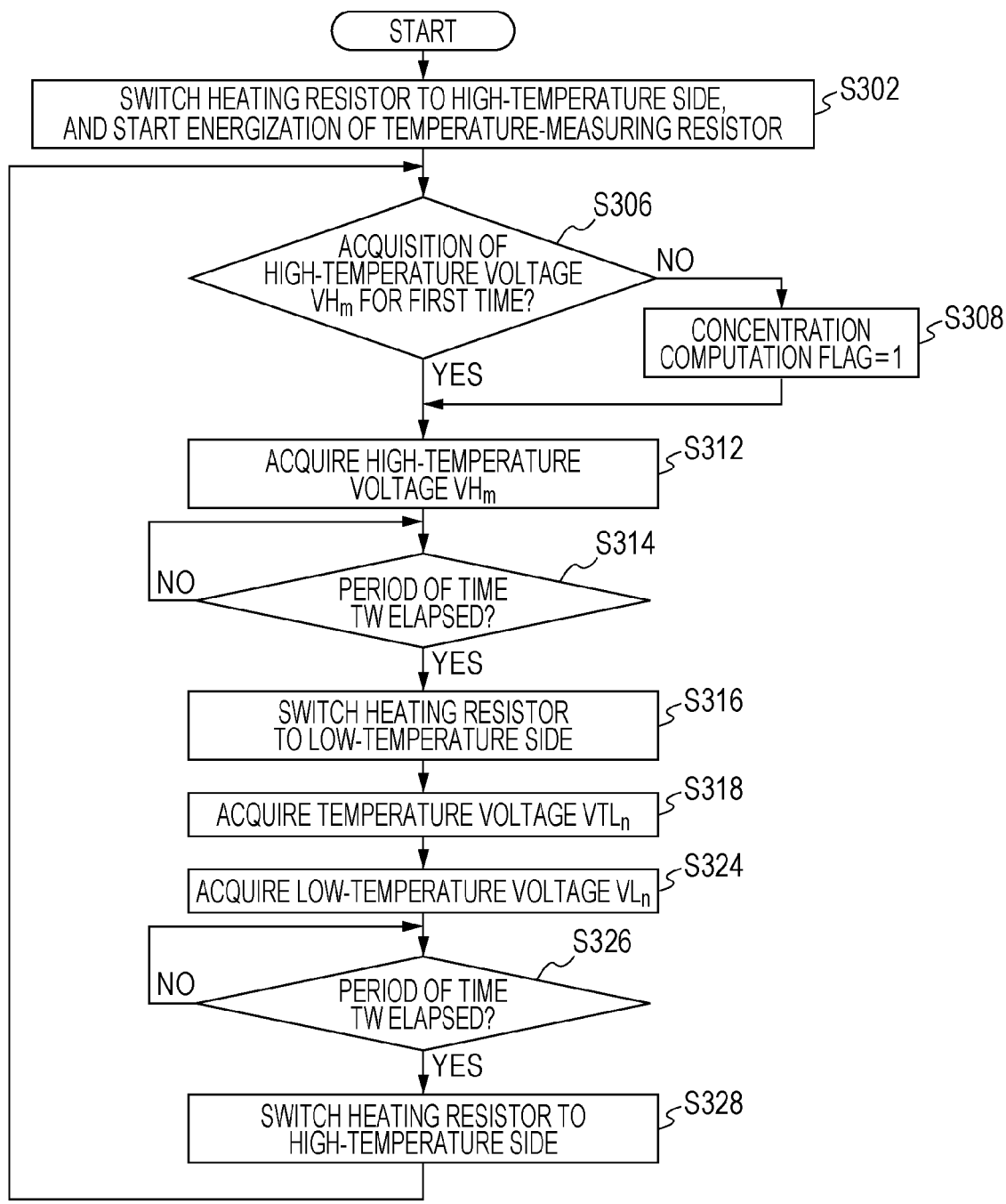
FIG. 8 is a flowchart of a process for acquiring VH, VL, and VT according to the second embodiment.
Figure 9:
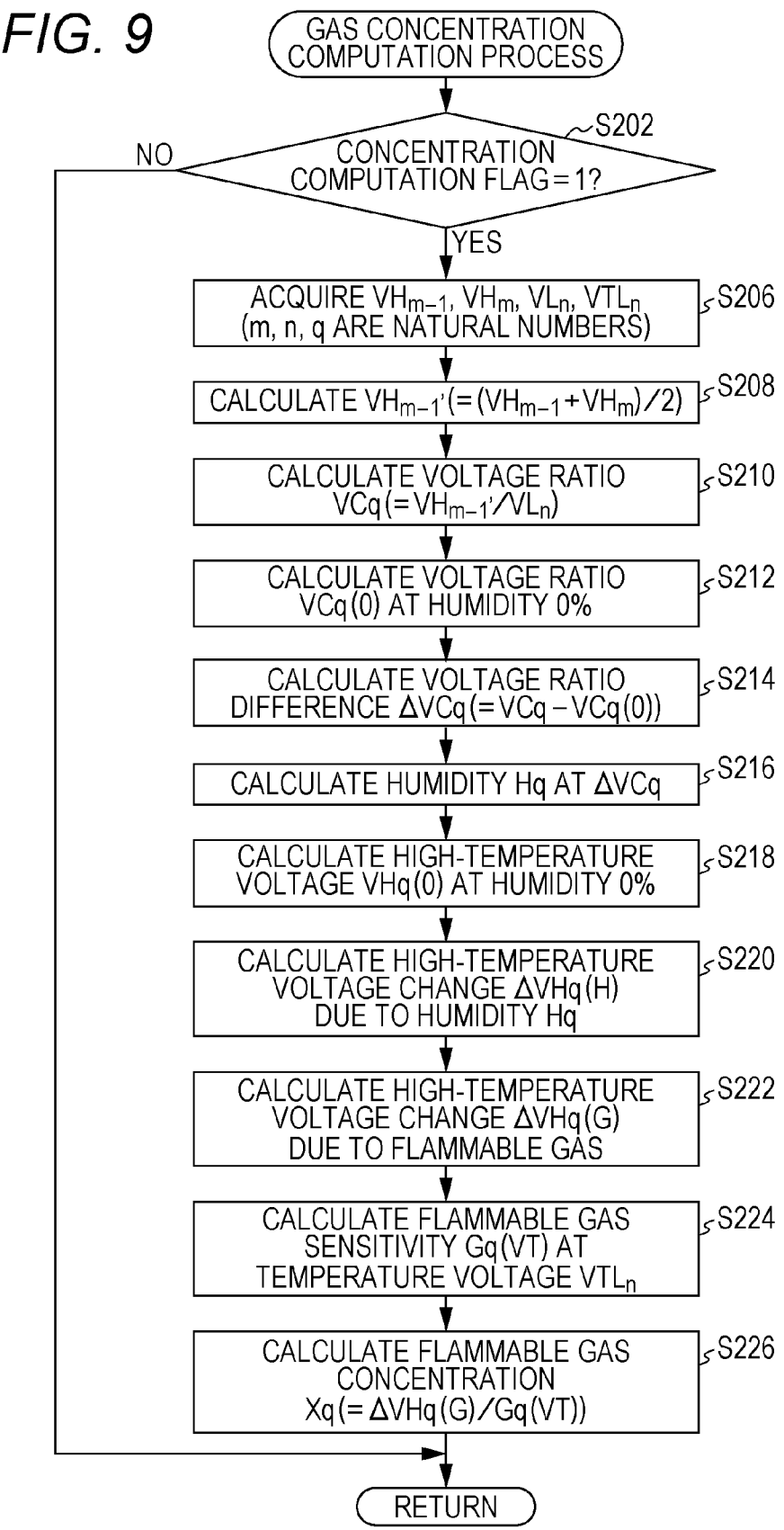
FIG. 9 is a flowchart of a gas concentration computation process using the average high temperature voltage VH' and the average low temperature voltage VL' according to the second embodiment.
Figure 10:
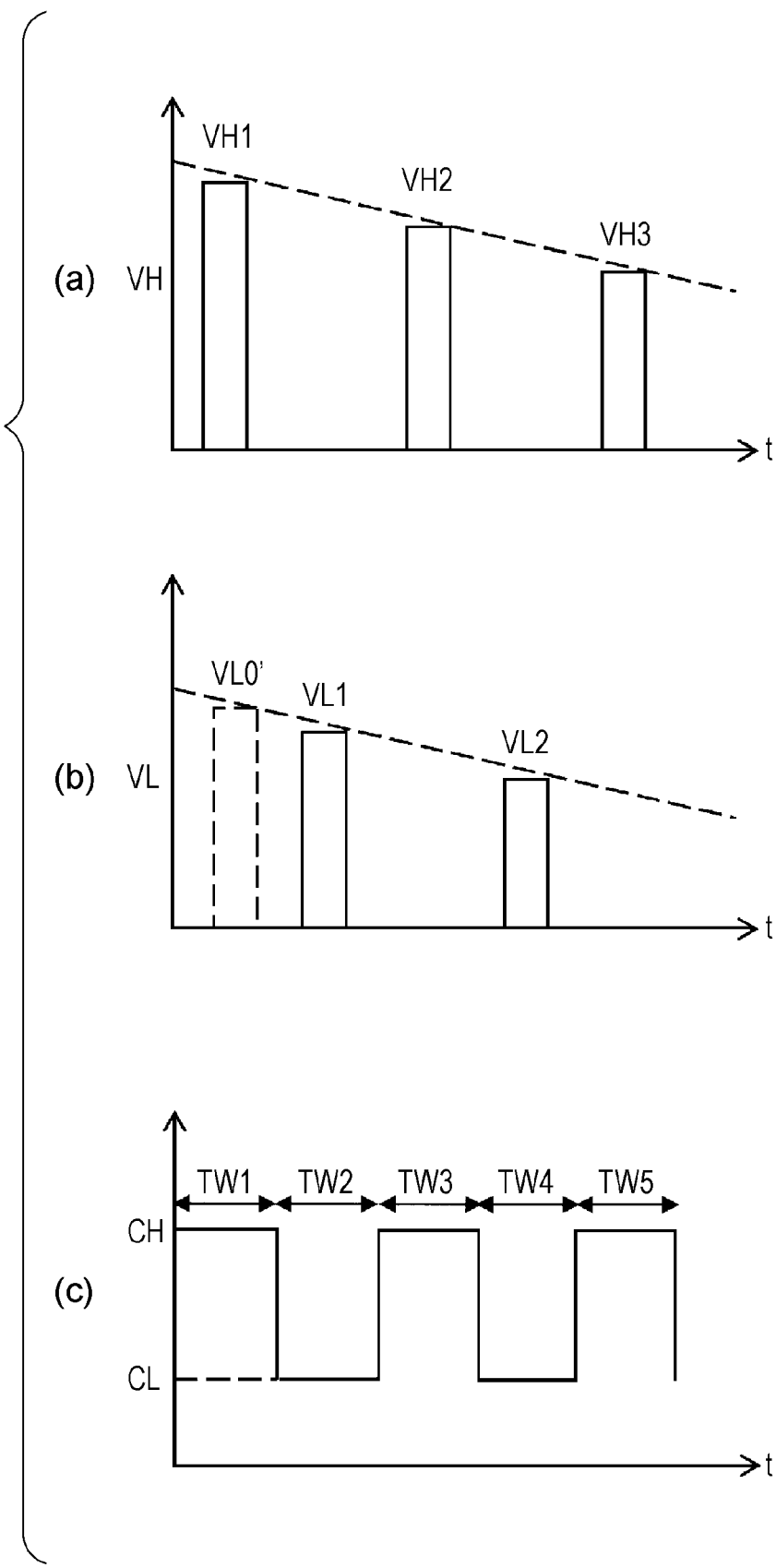
FIG. 10 shows time charts of the timing for acquiring VH and VL, and a time chart of the first set temperature (CH) and the second set temperature (CL) of the heating resistor in a conventional flammable gas detection apparatus.

With reference to FIGS. 7 to 9, the gas concentration computation process in the flammable gas detection apparatus according to the second embodiment of the present invention will be described.

FIG. 7 shows time charts of the timing for acquiring VH and VL (FIG. 7(a) and (b), respectively), a time chart indicating the first set temperature (CH) and the second set temperature (CL) of the heating resistor (FIG. 7(c)), and a time chart indicating the timing of acquiring the temperature (temperature voltage VT) of the temperature-measuring resistor (FIG. 7(d)). FIG. 8 is a flowchart of the process of acquiring VH, VL, and VT. FIG. 9 is a flowchart of the gas concentration computation process using the average high temperature voltage VH'.

As shown in FIG. 7, when the environment temperature is increased during detection, both VH and VL decrease over time (FIG. 7(a), (b)). Thus, when VH1 is detected in the initial period of time TW1 and then VL1 is detected in the next period of time TW2, the value of the low temperature voltage is decreased compared with if detected in the same timing (period of time TW1) as for VH1. Thus, according to the second embodiment, as in the first embodiment, the gas concentration is computed based on the first information group of the average high temperature voltage VH1' averaging the two temporally successive values of VH1 and VH2 in the periods of time TW1 and TW3, and VL1 in the period of time TW2 between VH1 and VH2. Here, VH and VL used in the first information group are indicated by an inverted triangular region R1 in FIG. 7.

Thus, because the predicted value (average high temperature voltage VH1') of the high temperature voltage in the same detection timing (period of time TW2) as for the low temperature voltage (VL1) is estimated from the high temperature voltages (VH1, VH2) in other periods of time TW1 and TW3, the voltage difference and voltage ratio of VH and VL at the same detection timing can be obtained, and the decrease in gas concentration detection accuracy accompanying a temporal change in environment temperature can be suppressed. Further, by using the environment temperature (temperature voltage VTL1) in the period of time TW2 in the first information group, the environment temperature at the same detection timing as the timing of calculation of the voltage difference and voltage ratio of VH and VL (the first information group) can be used for computing the gas concentration. Namely, in the gas concentration computation process according to the second embodiment, the gas concentration is computed based on the first information group including the average high temperature voltage VH1' averaging the values of the two temporally successive high temperature voltages VH1 and VH2; the low temperature voltage VL1 in the period of time TW2 between the two high temperature voltages VH1 and VH2; and the environment temperature VTL1 in the period of time TW2 in which the low temperature voltage VL1 is detected.

However, according to the second embodiment, after the first information group is calculated in the period of time TW3, the timing of calculating the first information group next time is the period of time TW5, which is two periods later. Herein, the VH and VL used for the first relationship calculated for the second time are indicated by an inverted triangular region R3 in FIG. 7. Thus, when only one of the first information group and the second information group is calculated, the first information group, i.e., the voltage difference and voltage ratio of VH and VL at same detection timing, is calculated in twice the period of time TW. As a result, although the gas concentration detection accuracy is decreased compared with the first embodiment, the processing burden for the microcomputer is advantageously decreased.

With reference to FIGS. 8 and 9, the process performed by the CPU of the microcomputer 7 for acquiring VH, VL, and VT, and the gas concentration computation process will be described.

As shown in FIG. 8, in the process for acquiring VH, VL, and VT, first in step S302, the CPU switches the heating resistor 34 to the high temperature side (the first set temperature (CH) side), and starts energization of the temperature-measuring resistor 35. Specifically, the CPU performs control to maintain the resistance value of the bridge circuit 51, i.e., the set temperature of the heating resistor 34, to the first set temperature CH during the regular period of time TW by the change-over signal CG1.

Then, in S306, the CPU determines whether the high temperature voltage (VHm) is acquired for the first time, i.e., whether it is VH1. If "No", "1" is allocated to the concentration computation flag (S308), and the process moves to S312. If "Yes" in S306, the process moves to S312. According to the second embodiment, the average low temperature voltage VLn-1' is not calculated and therefore the computation determination flag is not used.

Then, in S312, the CPU acquires the high temperature voltage (VHm) of the heating resistor 34 and determines whether the period of time TW has elapsed (S314). If "Yes" in S314, the process moves to S316. If "No", the process returns to S314 and waits for the elapse of TW. In the example of FIGS. 7 and 8, TW=200 msec.

Then, in S316, the CPU switches the heating resistor 34 to the low temperature side (the second set temperature (CL) side), and acquires the temperature voltage VTLn in the period of time of S316 (S318).

Then, in S324, the CPU acquires the low temperature voltage (VLn) of the heating resistor 34, and determines whether the period of time TW has elapsed (S326). If "Yes" in S326, the process moves to S328. If "No", the process returns to S326 and waits for the elapse of TW.

In S328, the CPU switches the heating resistor 34 to the high temperature side (the first set temperature (CH) side) and returns to S306.

The VHm, VLn, VTHm, and VTLn thus acquired are stored in the storage apparatus 8 (RAM) in association with the concentration computation flag and read in the following gas concentration computation process.

With reference to FIG. 9, the gas concentration computation process will be described. The gas concentration computation process is performed in each period of time TW. Namely, because the interval of S306 to S314 in FIG. 8 is processed in the period of time TW, the gas concentration computation process (mainly the calculation of the average high temperature voltage VHm-1') is performed upon the elapse of S314, and the gas concentration computation process (mainly the acquisition of VTLn and VLn) is also performed in the interval of S316 to S326 that is processed in the next period of time TW.

The process of FIG. 9 is the same as S206 to S226 of the process described with reference to FIG. 6 with the exception that step S204 is omitted and S202 directly moves to S206. Thus, the process of FIG. 9 is designated with the same step numbers and their description will be omitted.

The present invention is not limited to the foregoing embodiments, and it should be understood that numerous modifications and equivalents can be devised without departing from the spirit and scope of the invention. For example, the apparatus for storing the various programs or data for carrying out the processes in the microcomputer 7 are not limited to the storage apparatus 8 provided in the microcomputer 7, but may include any form of external storage apparatus or recording medium capable of communicating information with the microcomputer 7. In this case, the microcomputer 7 executes the various processes by using the various programs or data that it reads from the external storage apparatus or recording medium. Examples of the recording medium include a portable semiconductor memory (such as a USB memory or a memory card (registered trademark)), an optical disc such as a CD-ROM or a DVD, and magnetic disks.

DESCRIPTION OF REFERENCE NUMERALS

1: flammable gas detection apparatus
34: heating resistor
CH: first set temperature
CL: second set temperature
VH: high temperature voltage
VL: low temperature voltage
VH': average high temperature voltage
VL': average low temperature voltage
TW: period of time
T: environment temperature
7: microcomputer (energization control unit, gas concentration computation unit)
50: energization control circuit (energization control unit)
30: substrate
35: temperature-measuring resistor

The invention claimed is:

1. A flammable gas detection apparatus comprising:
a heating resistor disposed in an atmosphere for detection and whose resistance value is changed in response to a temperature change in the heating resistor;
an energization control unit that performs control to switch an energization state of the heating resistor at regular periods of time so that the heating resistor has resistance values respectively corresponding to preset two set temperatures;
a temperature-measuring resistor whose resistance value is changed by a change in an environment temperature which is the temperature in the atmosphere for detection; and
a gas concentration computation unit that computes a concentration of flammable gas in the atmosphere for detection by using a voltage across the heating resistor that is detected at the time of energization of the heating resistor by the control by the energization control unit, and the environment temperature based on a voltage change caused by a change in the resistance value of the temperature-measuring resistor,
wherein:
the two set temperatures include a first set temperature on a high temperature side and a second set temperature on a low temperature side;
the voltage across the heating resistor that is detected at the first set temperature is a high temperature voltage, and the voltage across the heating resistor that is detected at the second set temperature is a low temperature voltage; and
the gas concentration computation unit computes the concentration of the flammable gas based on a first information group including an average high temperature voltage averaging the values of two temporally successive high temperature voltages, the low temperature voltage in a period of time between the two high temperature voltages, and the environment temperature in the period of time in which the low temperature voltage is detected, or a second information group including an average low temperature voltage averaging the values of two temporally successive low temperature voltages, the high temperature voltage in a period of time between the two low temperature voltages, and the environment temperature in the period of time in which the high temperature voltage is detected.

2. The flammable gas detection apparatus as claimed in claim 1, wherein the gas concentration computation unit uses, as the low temperature voltage in the first information group, the second one of the two temporally successive low temperature voltages in the second information group, and, as the high temperature voltage in the second information group, the second one of the two temporally successive high temperature voltages in the first information group.

* * * * *